United States Patent [19]

Siebold

[11] Patent Number: Plant 7,569

[45] Date of Patent: Jun. 25, 1991

[54] BEGONIA PLANT NAMED GOLDEN ANNIVERSARY

[75] Inventor: Howard Siebold, Fort Bragg, Calif.

[73] Assignee: Golden State Bulb Growers, Watsonville, Calif.

[21] Appl. No.: 500,741

[22] Filed: Mar. 28, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new Begonia plant named Golden Anniversary, characterized by its distinct fragrance, fully double male flowers, rich apricot petal color at its center, changing to a brighter yellow-orange in the center and then to a generally coral color at the edge, its full and pendulous habit, and its floriferousness.

2 Drawing Sheets

The present invention relates to a new and distinctive cultivar of Begonia plant known by the cultivar name Golden Anniversary.

The new cultivar was discovered by the inventor Howard Siebold as a seedling from a controlled crossing by the inventor of an unnamed *Tuberhybrida pendula* as a pollen parent with the cultivar Yellow Sweety as the seed parent.

Asexual reproduction by the inventor by leaf cuttings has reproduced the unique features of the new cultivar through successive propagations.

The following characteristics distinguish the new begonia from both its parents and other Begonias commercially known and used in the floriculture industry.

1. The flowers have a definite and distinct fragrance that can be described as gently sweet but not overpowering. It is often compared to the scent of a fragrant rose bloom. The fragrance is most pronounced when the temperature is between 70° and 80° F.

2. The male flowers are fully double and do not produce pollen or visible male reproductive parts under normal growing conditions.

3. The main flower color is golden aprioct, with the back of the exterior petals tinged red under full sun conditions. The petal edges are a distinct coral, with the petal color changing from the edge to a bright yellow-orange approaching the center, to a darker apricot color at the very center. This color variation and gradation are unique.

4. The plant habit is full and pendulous with numerous flowering shoots (5–6 or more). Each flowering shoot will produce anywhere from 4–5 peduncles with 1 or 2 male flowers on each during the course of a growing season.

There are no Begonia cultivars with which the new cultivar can be meaningfully compared. The variance and gradation of color is unique, as is the distinct fragrance.

The accompanying colored photographs taken Aug. 24, 1989 illustrate the new cultivar.

The photograph at the top of sheet 1 is a front perspective view showing a typical plant of Golden Anniversary grown in a 10″ pot. The photograph at the bottom of sheet 1 is an enlarged showing of a typical flower.

the photograph on sheet 2 illustrates the upper and under sides of typical leaves. The photographs depict the colors as true as it is reasonably possible to obtain in colored reproductions of this type.

The following is a detailed description of my new Begonia cultivar based on plants produced under commercial practices in Capitola, Calif. Color references are made to The Royal Horticultural Society Colour Chart except where general terms of ordinary dictionary significance are used.

Parentage: The begonia cultivar Yellow Sweety (seed parent) × unnamed *Tuberhybrida pendula* (pollen parent).

Propagation:

(A) *Type cutting.*—Leaf cuttings.

(B) *Time to root.*—24–30 days at 21° C. summer; 32–38 days at 21° C. winter.

(C) *Rooting habit.*—Abundant, fibrous, dendritic.

(D) *Time for shoot development.*—Slow; 10–14 weeks in summer and up to 16 weeks in winter. Shoot count is medium to high in summer and less in winter.

Plant description:

(A) *Form.*—Low, mounding, pendulous form; herbaceous.

(B) *Habit of growth.*—Slow, uniform growth with numerous shoots and good branching habit. At full growth the plant is well rounded with about a 18–24″ height and equal width with pendulous flowering shoots.

(C) *Foliage.*—Simple, alternate, and borne on semi-rigid 6–8″ petioles. (1) Size: At maturity the leaves reach 10–12″ from base to apex, and at their widest point the leaves are up to 7″ across. (2) Shape: Broad-ovate, obliquely cordate, broadly acuminate with rounded basal lobes. (3) Texture: Firm, crisp, but not brittle; hirtellous on both surfaces with a ciliate tendency on bottom surface. (4) Margin: Doubly serrate. (5) Color: Young foliage: Top side slightly darker than 143A; under side 147C. Mature foliage: Top side 146A and B; under side 147C. (6) Veination: Reticulate.

Flowering description:

(A) *Flowering habits.*—Flowering is presented on a semi-pendulous raceme. Often, but not always, secondary male and female flowers will develop below the primary flowers. Some peduncles will have a single male flower with a solitary female flower, while others will have matching female flowers per male.

(B) *Natural flowering season.*—The natural flowering season is the summer and fall months.

(C) *Flower buds.*—Flat, nearly round, tending towards bell shaped.

(D) *Flowers borne.*—On small pedicels originating from long ($7\frac{1}{2}''$ to $8\frac{1}{2}''$) axillary peduncles, resulting in a solitary male and one or two female flowers, and occasionally a secondary male and female flower as raceme develops.

(E) *Quantity.*—Flowering ranges from 2–5 flowers per peduncle and numerous (3–5) peduncles per shoot, with 4–6 shoots per plant.

(F) *Tepals.*—(1) Shape: Oval to rear drop shaped. (2) Color: Top side in spring/summer when opening, golden orange, 38A at petal edge, changing to 15A toward petal center, and apricot, approximately 23 C., at center; under side 37D near edge, changing to 37B toward center and 24C at center. (3) Number of tepals: 45–56 on male flowers, 5 on female flowers. (4) Size of tepals: Outer (male), up to $2\frac{3}{4}''\times2\frac{3}{4}''$, inner $\frac{3}{8}''\times\frac{3}{8}''$; $1\frac{1}{2}''\times1\frac{3}{4}''$ to $1\frac{5}{8}''\times2''$ (female). (5) Flower size: Male, $5''\times5''$; female, $4''\times4''$.

(G) *Reproductive organs.*—(1) Stamens: None. (2) Pistils: (a) Stigma shape: Multi-lobed; color 15A. (b) Style color: 15A. (c) Ovaries: Three in number, syncarpous; $\frac{3}{8}''$–$\frac{5}{8}''$ in total size; pale green (142C) in color with sheen on exterior.

Disease resistance: Golden Anniversary has shown excellent disease resistance to date.

I claim:

1. A new and distinct Begonia plant named Golden Anniversary, as illustrated and described.

* * * * *

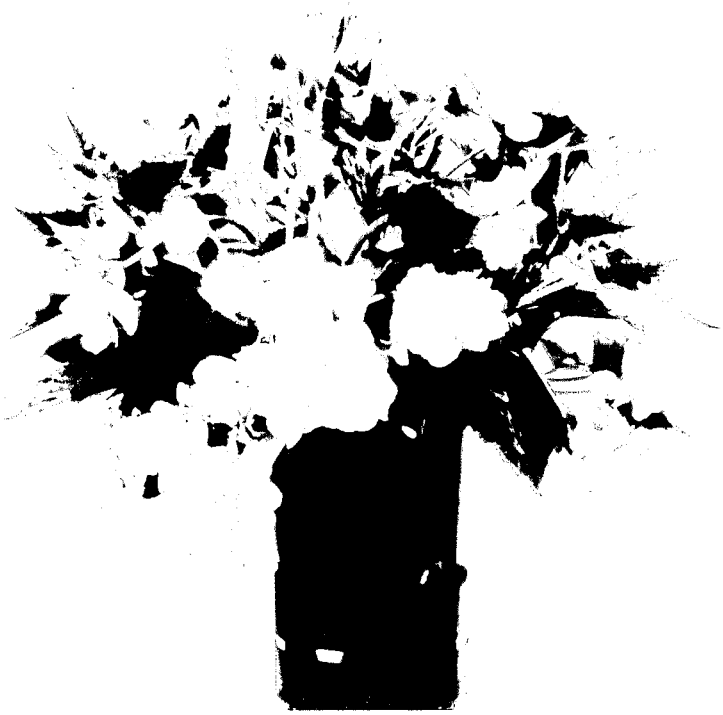

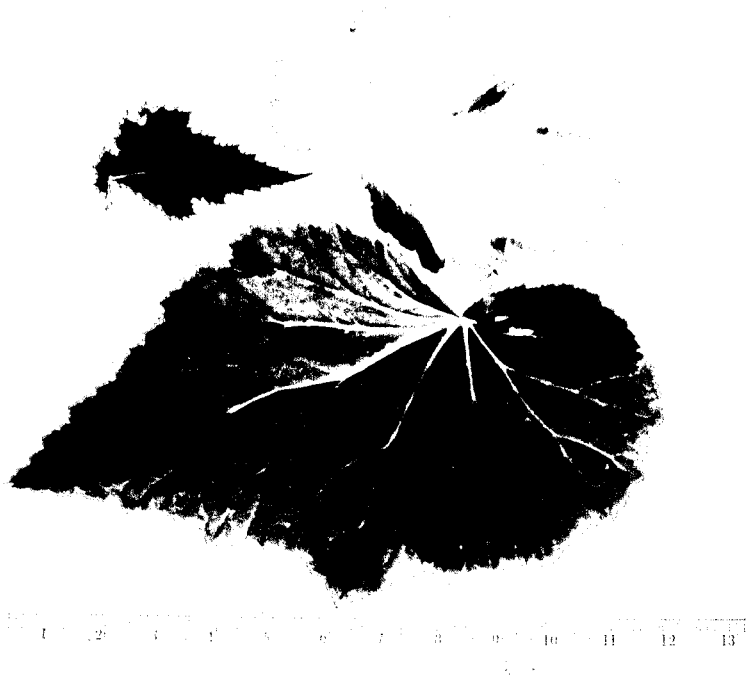
1
2
3
4
5
6
7
8
9
10
11
12
13